(12) United States Patent
Chuman et al.

(10) Patent No.: US 6,476,624 B1
(45) Date of Patent: Nov. 5, 2002

(54) CRACK MONITORING METHOD AND APPARATUS

(75) Inventors: Yasuharu Chuman; Masafumi Yamauchi; Nobuhiko Nishimura; Masahiro Umata, all of Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/699,415

(22) Filed: Oct. 31, 2000

(30) Foreign Application Priority Data

Nov. 16, 1999  (JP) ............................. 11-325273

(51) Int. Cl.⁷ ..................... G01R 27/08; G01R 31/08; G01R 31/02
(52) U.S. Cl. ..................... 324/718; 324/716; 324/522; 324/761
(58) Field of Search ................. 324/718, 715, 324/716, 713, 721, 761, 758, 515, 522

(56) References Cited

U.S. PATENT DOCUMENTS

| 4,683,419 A | | 7/1987 | Neuelmann et al. | |
| 4,764,970 A | * | 8/1988 | Hayashi | 382/149 |
| 5,138,269 A | * | 8/1992 | Deutsch | 324/715 |
| 5,202,641 A | * | 4/1993 | Unvala | 324/715 |
| 5,227,731 A | * | 7/1993 | Prabhakaran et al. | 324/718 |

FOREIGN PATENT DOCUMENTS

JP         A 61-80039         4/1986

* cited by examiner

Primary Examiner—N. Le
Assistant Examiner—Anjan K. Deb
(74) Attorney, Agent, or Firm—Birch, Stewart, Kolasch & Birch, LLP

(57) ABSTRACT

A method and apparatus for monitoring crack inside piping suitable for high temperature environment including an electrode attachment process for attaching a pair of heat resistant current input-output electrodes to an outer circumferential surface of the piping such that the crack is positioned between electrodes. Measuring intra-crack potential difference by a pair of heat resistant potential difference measuring electrodes attached to outer circumferential surface of the piping and placed between the input output electrodes by supplying alternating current between the input-output electrodes. Crack length is calculated from the measured electric potential difference after correcting the intra-crack electric potential difference as a function pipe temperature and pressure by an intra-crack electrode potential difference correction process.

22 Claims, 9 Drawing Sheets

Distance W between power input-output electrodes

CRACK MONITORING METHOD AND APPARATUS

BACKGROUND OF THE INVENTION

1. Field of the Invention

The present invention relates to a crack monitoring method and apparatus for monitoring the length of a crack generated inside a weld in high-temperature thick-walled piping of a plant while the plant continues to operate.

2. Related Background Art

In an electric power station or the like, a periodic inspection is performed of welds and the like in high-temperature thick-walled piping, for example, a main steam pipe (Thickness: Approx. 100 mm) or a high-temperature reheat steam pipe (Thickness: Approx. 30 to 40 mm) of a plant in a non-destructive test method such as an ultrasonic test (UT) method or a time of flight diffraction (TOFD) method to check for the presence or absence of a crack and its length.

If a crack is found during the periodic inspection, the probable life of the piping is calculated on the basis of the length of the crack and the operating conditions of the plant to make a repair plan while the piping is used as it is until the plant is repaired since it is very hard to replace the cracked piping immediately.

As set forth in the above, the probable life of the cracked piping is calculated on the basis of the size of the crack and the operating conditions of the plant, and therefore while the plant can continue to be used without any problem within this probable life of the pipe, it may be changed by a growth rate change of the crack being caused for some reason. Therefore, to secure safety, it is desired to obtain a capability of monitoring the status of the crack during the operation of the plant. In the above UT or TOFD method, however, a probe cannot be used in a high-temperature environment (500 to 600), and therefore it has been impossible to apply those methods to the monitoring in the above.

SUMMARY OF THE INVENTION

In view of this problem, it is an object of the present invention to provide a crack monitoring method and apparatus which is capable of monitoring a crack inside piping precisely and easily at all times even in a high-temperature environment during the operation of a plant.

According to a first aspect of the present invention to solve the above problem, there is provided a crack monitoring method for monitoring a crack inside piping, comprising attaching a pair of heat-resistant current input-output electrodes to an outer circumferential surface of the piping such that the crack whose position is previously specified is put between the pair of heat-resistant current input-output electrodes and attaching at least one pair of heat-resistant crack electric potential difference measuring electrodes to the outer circumferential surface of the piping such that they are put between the current input-output electrodes, supplying an alternating current between the current input-output electrodes and measuring an electric potential difference between the crack electric potential difference measuring electrodes, correcting the electric potential difference between the crack electric potential difference measuring electrodes, and calculating the length of the crack on the basis of the electric potential difference obtained and corrected.

According to a second aspect of the present invention, there is provided a crack monitoring method according to the first aspect of the invention, wherein the attached positions of the current input-output electrodes and the crack electric potential difference measuring electrodes are set on the basis of an electric field analysis of the portion of the welded portion of the piping surrounding the crack so that the electric potential difference can be measured most sensitively at a growth of the crack in the piping.

According to a third aspect of the present invention, there is provided a crack monitoring method according to the second aspect of the invention, wherein a pair of crack electric potential difference measuring electrodes are attached to the piping such that the crack on the center side is put between the electrodes in a direction perpendicular to the direction of likely growth of the crack in the piping.

According to a fourth aspect of the present invention, there is provided a crack monitoring method according to the third aspect of the invention, wherein the other pair of crack electric potential difference measuring electrodes are attached to the piping such that the crack on the tip side thereof in the direction of likely growth is put between the electrodes in a direction perpendicular to the direction of likely growth of the crack in the piping.

According to a fifth aspect of the present invention, there is provided a crack monitoring method according to the first aspect of the invention, wherein the current input-output electrodes and the crack electric potential difference measuring electrodes are removably attached to an outer circumferential surface of the piping.

According to a sixth aspect of the present invention, there is provided a crack monitoring method according to the first aspect of the invention, wherein an alternating current of a frequency of 10 Hz or less is supplied between the current input-output electrodes.

According to a seventh aspect of the present invention, there is provided a crack monitoring method according to the first aspect of the invention, wherein an alternating current of a frequency of 50 Hz or greater is supplied between the current input-output electrodes.

According to an eighth aspect of the present invention, there is provided a crack monitoring method according to the first aspect of the invention, wherein an alternating current of a frequency of either 10 Hz or less or 50 Hz or higher are supplied alternately between the current input-output electrodes.

According to a ninth aspect of the present invention, there is provided a crack monitoring method according to the first aspect of the invention, wherein the intra-crack electric potential difference correction process is used to correct the electric potential difference between the crack electric potential difference measuring electrodes on the basis of the electric potential difference between the pair of heat-resistant correction electric potential difference measuring electrodes attached to the outer circumferential surface of the piping.

According to a tenth aspect of the present invention, there is provided a crack monitoring method according to the first aspect of the invention, wherein the intra-crack electric potential difference correction process is used to correct the electric potential difference between the crack electric potential difference measuring electrodes on the basis of the temperature of the piping.

According to an 11th aspect of the present invention, there is provided a crack monitoring method according to the first aspect of the invention, wherein the intra-crack electric potential difference correction process is used to correct the electric potential difference between the crack electric potential difference measuring electrodes on the basis of the internal pressure of the piping.

According to a 12th aspect of the present invention, there is provided a crack monitoring method according to the first aspect of the invention, wherein the crack length calculation process is used to calculate the length of the crack from the electric potential difference obtained by the intra-crack electric potential difference correction process on the basis of a correlation between the length of the crack obtained from an electric field analysis of a surrounding portion of the welded portion of the piping containing the crack or experimentally and the electric potential difference in the crack.

According to a 13th aspect of the present invention, there is provided a crack monitoring method according to the first aspect of the invention, wherein the crack length calculation process further comprises a first step of obtaining a correlation between the maximum crack length of the crack for each stress change and an electric potential difference change in the crack on the basis of the electric field analysis of the portion of the welded portion of the piping surrounding the crack in the piping or experimentally, a second step of obtaining a stress change between two points in time, that is, the time when a high load is applied and the time when a low load is applied on the piping on the basis of the temperature and the internal pressure of the piping, and a third step of obtaining a length $2a$ of the crack corresponding to the stress change from the electric potential difference change between the above two points of time.

On the other hand, to solve the above problem, according to a 14th aspect of the present invention, there is provided a crack monitoring apparatus for monitoring a crack generated inside the piping, comprising a pair of current input-output electrodes made of heat-resistant material attached to an outer circumferential surface of the piping, a sensor head having at least one pair of crack electric potential difference measuring electrodes made of heat-resistant material attached to the outer circumferential surface of the piping such that they are put between the current input-output electrodes, an electric alternating current power supply for supplying an alternating current between the current input-output electrodes of the sensor head, a crack electric potential difference measurement means for measuring the electric potential difference between the crack electric potential difference measuring electrodes of the sensor head, an intra-crack electric potential difference correction means for correcting an electric potential difference between the crack electric potential difference measuring electrodes of the sensor head measured by the crack electric potential difference measurement means, and a crack length calculation means for calculating a length of the crack on the basis of the electric potential difference obtained by the intra-crack electric potential difference correction means.

According to a 15th aspect of the present invention, there is provided a crack monitoring apparatus according to the 14th aspect of the invention, wherein the positions of the current input-output electrodes and those of the crack electric potential difference measuring electrodes of the sensor head are set on the basis of an electric field analysis of the portion of the welded portion of the piping surrounding the crack in the piping so that the electric potential difference can be measured most sensitively at the growth of the crack in the piping.

According to a 16th aspect of the present invention, there is provided a crack monitoring apparatus according to the 15th aspect of the invention, wherein the pair of crack electric potential difference measuring electrodes of the sensor head are attached to the piping such that the crack on the center side is put between the electrodes in a direction perpendicular to the direction of the likely growth of the crack in the piping.

According to a 17th aspect of the present invention, there is provided a crack monitoring apparatus according to the 16th aspect of the invention, wherein the other pair of crack electric potential difference measuring electrodes of the sensor head are attached to the piping such that the crack on the tip side thereof in the direction of likely growth is put between the electrodes in a direction perpendicular to the direction of likely growth of the crack in the piping.

According to a 18th aspect of the present invention, there is provided a crack monitoring apparatus according to the 14th aspect of the invention, wherein there is provided an attachment means for removably attaching the sensor head to the outer circumferential surface of the piping.

According to a 19th aspect of the present invention, there is provided a crack monitoring apparatus according to the 14th aspect of the invention, wherein an alternating current of a frequency of 10 Hz or less is supplied by the alternating current power supply.

According to a 20th aspect of the present invention, there is provided a crack monitoring apparatus according to the 14th aspect of the invention, wherein an alternating current of a frequency of 50 Hz or greater is supplied by the alternating current power supply.

According to a 21st aspect of the present invention, there is provided a crack monitoring apparatus according to the 14th aspect of the invention, wherein an alternating current which is alternately either 10 Hz or less or 50 Hz or higher is supplied by the alternating current power supply.

According to a 22nd aspect of the present invention, there is provided a crack monitoring apparatus according to the 14th aspect of the invention, wherein the intra-crack electric potential difference correction means comprises a pair of correction electric potential difference measuring electrodes made of heat-resistant material arranged in the sensor head so as to be attached to the outer circumferential surface of the piping and the correction electric potential difference measurement means for measuring an electric potential difference between the correction electric potential difference measuring electrodes.

According to a 23rd aspect of the present invention, there is provided a crack monitoring apparatus according to the 14th aspect of the invention, wherein the intra-crack electric potential difference correction means comprises a piping temperature measurement means for measuring temperature of the piping.

According to a 24th aspect of the present invention, there is provided a crack monitoring apparatus according to the 14th aspect of the invention, wherein the intra-crack electric potential difference correction means comprises a means for measuring the internal pressure of the piping.

According to a 25th aspect of the present invention, there is provided a crack monitoring apparatus according to the 14th aspect of the invention, wherein the crack length calculation means calculates the length of the crack from the electric potential difference obtained by the intra-crack electric potential difference correction means on the basis of a correlation between the length of the crack obtained from an electric field analysis of the welded portion of the piping surrounding the crack or experimentally and the electric potential difference in the crack.

According to a 26th aspect of the present invention, there is provided a crack monitoring apparatus according to the 14th aspect of the invention, wherein the crack length calculation means performs a first step of obtaining a correlation between the maximum crack length of the crack for each stress change and an electric potential difference change in the crack on the basis of the electric field analysis of the welded portion surrounding the crack in the piping or experimentally, a second step of obtaining a stress change between two points in time, that is, the time when a high load is applied and the time when a low load is applied on the piping on the basis of the temperature and the internal pressure of the piping, and a third step of obtaining the length of the crack corresponding to the stress change from the electric potential difference change between the above two points of time.

According to a 27th aspect of the present invention, there is provided a crack monitoring apparatus according to the 14th aspect of the invention, wherein a plurality of sensor heads are arranged, the intra-crack electric potential difference measurement means measures the electric potential differences between the crack electric potential difference measuring electrodes of each of the plurality of sensor heads, the intra-crack electric potential difference correction means corrects the electric potential differences between the crack electric potential difference measuring electrodes of the plurality of sensor heads measured by the crack electric potential difference measurement means, and the crack length calculation means calculates the lengths of the cracks on the basis of the electric potential differences obtained by the intra-crack electric potential difference correction means.

According to a 28th aspect of the present invention, there is provided a crack monitoring apparatus according to the 14th aspect of the invention, wherein the intra-crack electric potential difference measurement means, the intra-crack electric potential difference correction means, and the crack length calculation means are arranged in a remote area far from the piping.

DETAILED DESCRIPTION OF THE PREFERRED EMBODIMENTS

While a description will be given below for various embodiments of a crack monitoring method and apparatus according to the present invention, the invention is not limited to the following embodiments.

First Embodiment

A first embodiment of a crack monitoring method and apparatus according to the present invention will be described below by referring to FIGS. 1 to 5. Referring respectively to FIGS. 1, 2, 3, 4, and 5, there are shown a schematic diagram of the crack monitoring apparatus attached to the side of piping, an enlarged sectional view of the portion of the apparatus indicated by the arrow II in FIG. 1, a schematic diagram of another example of the main portion of FIG. 1, an explanatory diagram of the arrangement of electrodes, and a schematic diagram of the crack monitoring apparatus as located in a centralized control room.

Figure 1:
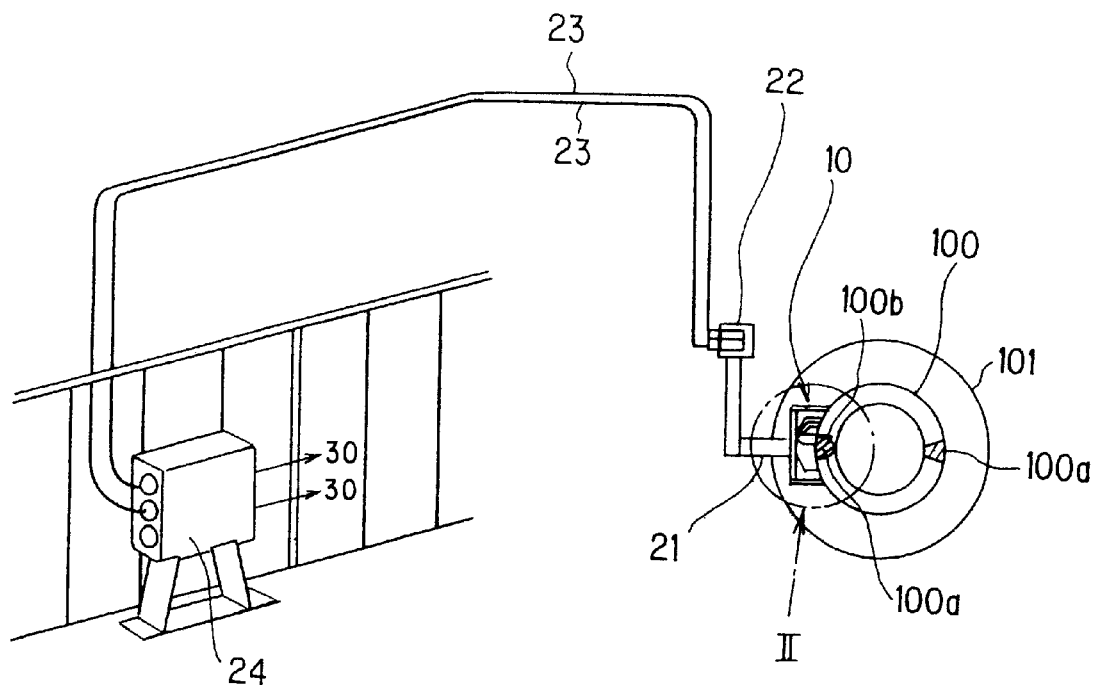
FIG. 1 is a schematic diagram of a crack monitoring apparatus mounted on the side of piping according to a first embodiment of the crack monitoring apparatus of the present invention.
Figure 2:
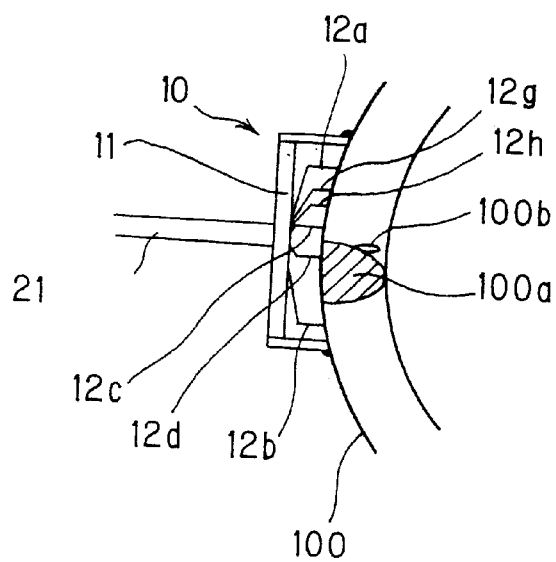
FIG. 2 is an enlarged sectional view of the portion of the apparatus of FIG. 1 taken along the arrow II.
Figure 4:
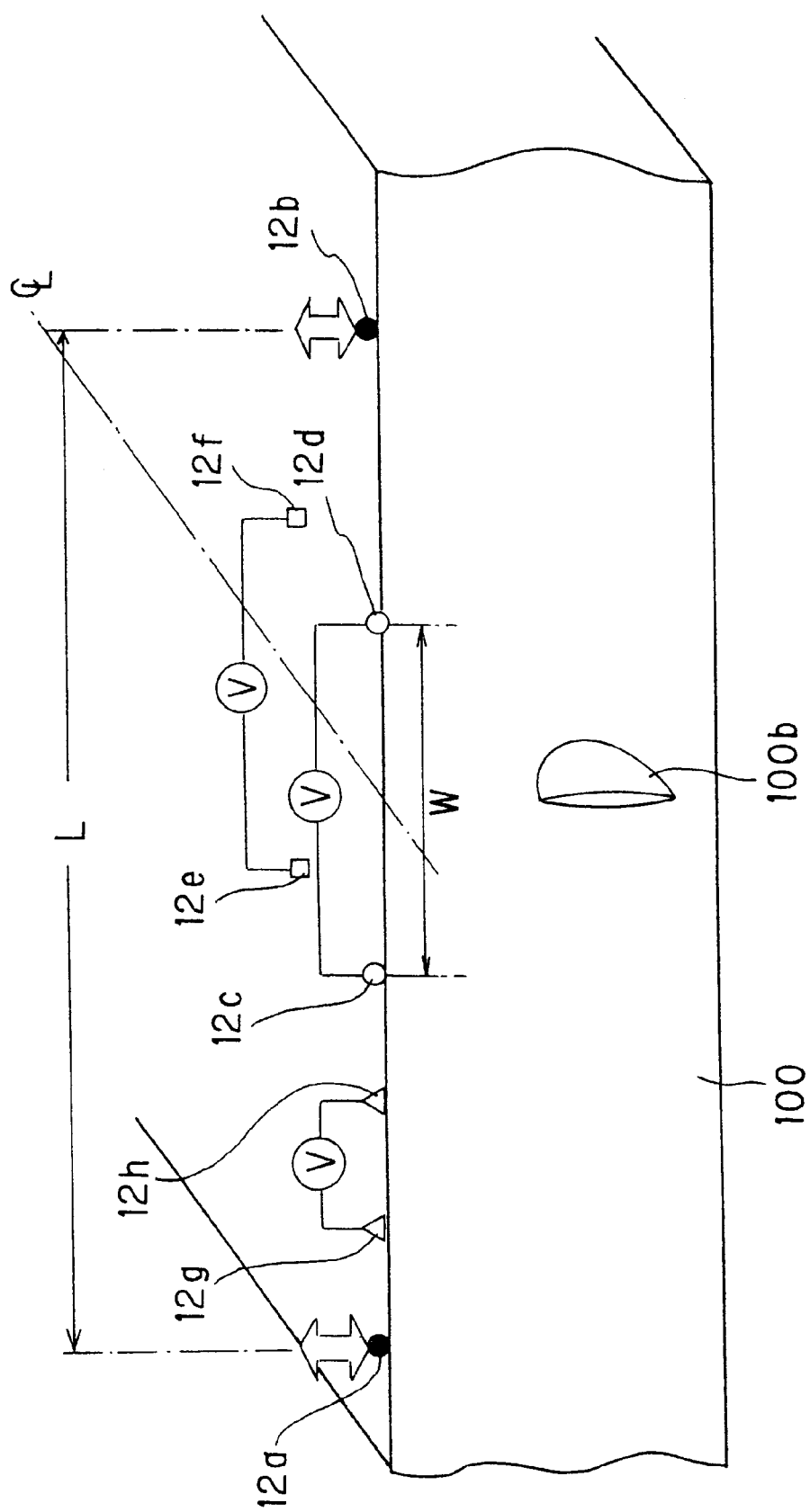
FIG. 4 is an explanatory diagram of the arrangement of electrodes.

As shown in FIGS. 1, 2, and 4, the crack monitoring apparatus according to this embodiment is applied to monitoring of a crack 100b that has occurred inside a weld 100a of high-temperature thick-walled piping 100 (for example, a main steam pipe (Thickness: Approx. 100 mm) or a high-temperature reheat steam pipe (Thickness: Approx. 30 to 40 mm)) of a power station plant or the like.

As shown in FIGS. 1, 2, and 4, a protective box 11 contains a current input electrode 12a made of a heat-resistant material (for example, Inconel) for inputting alternating current, a current output electrode 12b made of a heat-resistant material (for example, Inconel) for outputting an alternating current, two pairs of crack electric potential difference measuring electrodes 12c to 12f made of a heat-resistant material (for example, Inconel), and a pair of correction electric potential difference measuring electrodes 12g and 12h made of a heat-resistant material (for example, Inconel). The positions of these electrodes 12a to 12h are set on the basis of an electric field analysis of the surrounding portion of the crack 100b on the piping 100 so that an electric potential difference can be measured most sensitively at an area of likely growth of the crack 100b.

In other words, as shown in FIG. 4, the crack electric potential difference measuring electrodes 12c and 12d are attached to the protective box 11 in such a way that the crack 100b on the center side is put between the electrodes in a direction (a crosswise direction) perpendicular to the direction of likely growth (a lengthwise direction) of the crack 100b of the high-temperature thick-walled piping 100 and the crack electric potential difference measuring electrodes 12e and 12f are attached to the protective box 11 in such a way that the direction of likely growth of the crack 100b on the tip side thereof is put between the electrodes in a direction that perpendicular to the direction of likely growth (a lengthwise direction) of the crack 100b.

Specifically, the current input-output electrodes 12a and 12b are linearly arranged at an interval of a regulated length L (for example, 150 mm). One pair of crack electric potential difference measuring electrodes 12c and 12d are arranged in an identical straight line in the central portion between the current input-output electrodes 12a and 12b at an interval of a regulated length W (for example, 40 mm). The other pair of crack electric potential difference measuring electrodes 12e and 12f are spaced a predetermined interval (for example, 15 mm) away from the above pair of crack electric potential difference measuring electrodes 12c and 12d so as to be adjacent thereto. The correction electric potential difference measuring electrodes 12g and 12h are arranged along the same straight line, but are placed toward the current input electrode 12a between the current input-output electrodes 12a and 12b at an interval of a regulated length (for example, 20 mm). This protective box 11 and the electrodes 12a to 12h form a sensor head 10 in this embodiment.

Figure 3:
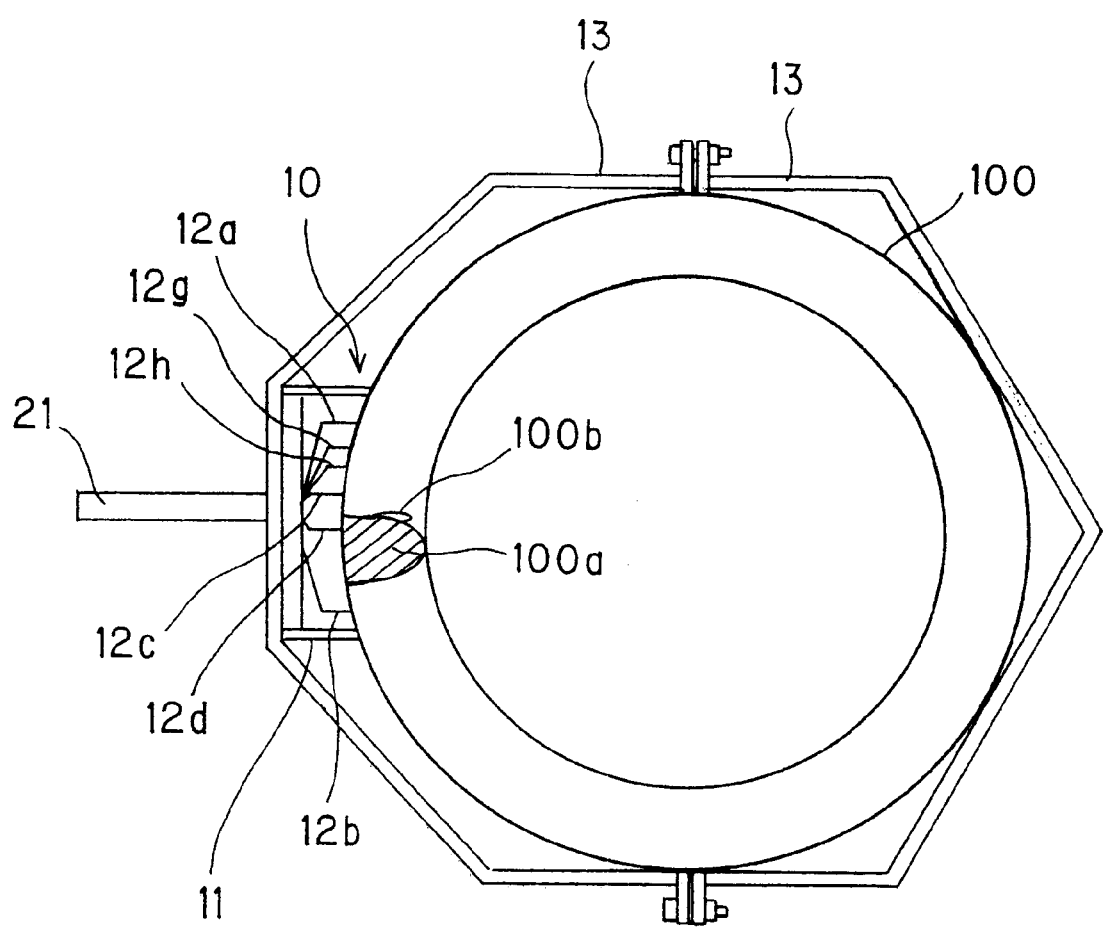
FIG. 3 is a schematic diagram of another example of the main portion of the piping in FIG. 1.

While the protective box 11 can be affixed permanently to the outer circumferential surface of the piping 100 by welding for an attachment of the sensor head 10. However, this method causes a problem regarding any potential of later removal of the sensor. Therefore, it is preferable to use a belt 13 made of steel as a fixing means, for example, as shown in FIG. 3 to fasten the protective box 11 removably around the outer circumferential surface of the piping 100. In FIG. 1, there is shown a lagging material 101.

As shown in FIGS. 1 and 2, the protective box 11 is coupled to an end of a lead-out tube 21. The other end of the lead-out tube 21 is coupled to a terminal box 22. The terminal box 22 is connected to ends of shield cables 23. The above various electrodes 12a to 12h of the sensor head 10 are connected to respective ends of the shielded cables 23 in the terminal box 22 via conductor wires which are not shown but which are inside the lead-out tube 21. The other ends of the shielded cables 23 are electrically connected to a centralized control room 30 in a remote area far from the piping 100 via a repeater 24.

Figure 5:
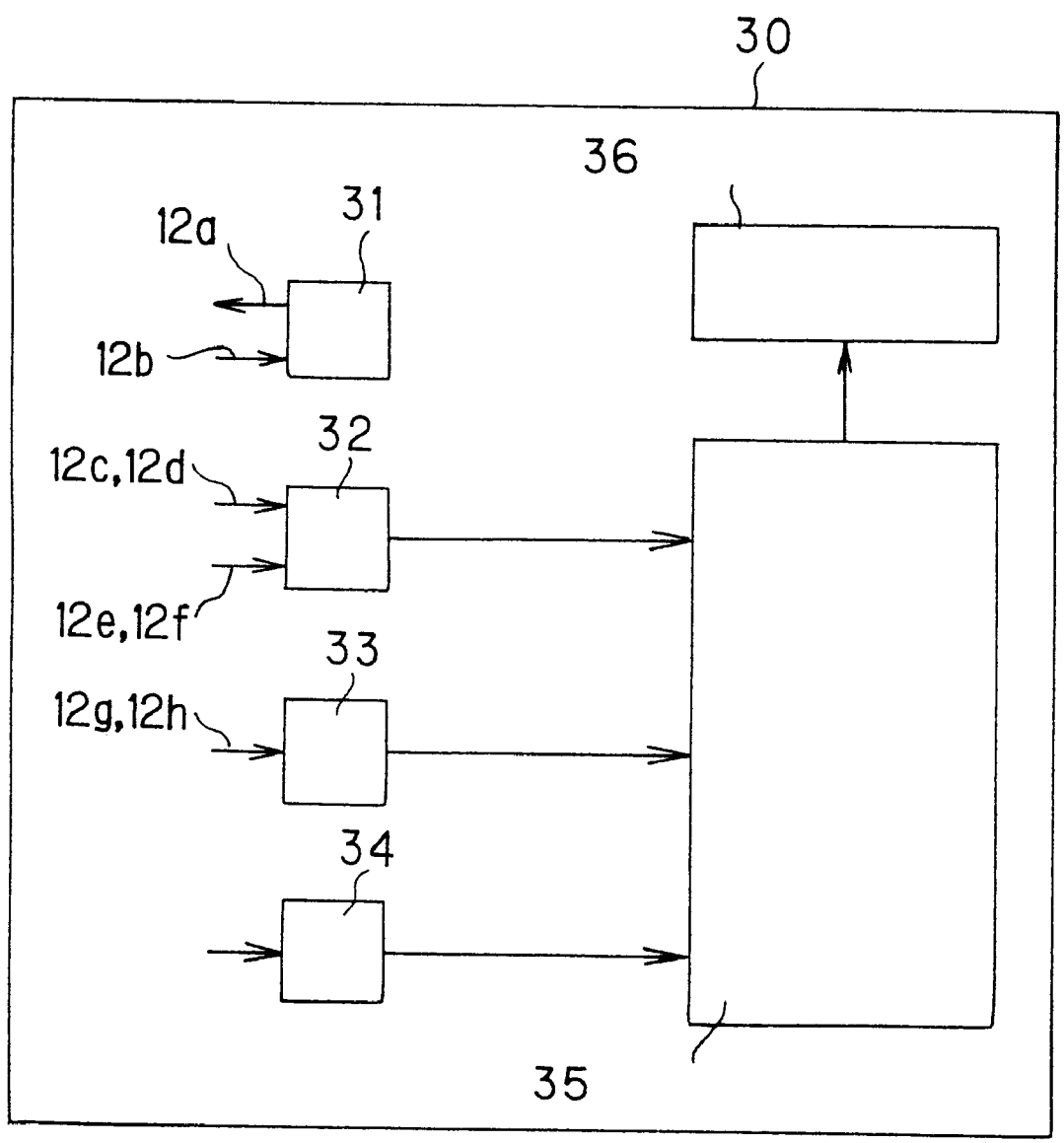
FIG. 5 is a schematic diagram of the crack monitoring apparatus as located in a centralized control room.

As shown in FIG. 5, the centralized control room 30 contains an alternating power supply 31 for supplying alternating current of a predetermined frequency between the current input-output electrodes 12a and 12b of the sensor head 10, a crack potentiometer 32 which is a crack electric potential difference measurement means for measuring electric potential differences between the crack measuring electrodes 12c and 12d and between the crack measuring electrodes 12e and 12f, and a correction potentiometer 33 which is a correction electric potential difference measuring means for measuring the electric potential difference between the correction electric potential difference measuring electrodes 12g and 12h, which are electrically connected to the above shielded cables 23 via the repeater 24, respectively.

In addition, the centralized control room 30 contains a correction arithmetic unit 35 for correcting the electric potential differences obtained by the crack potentiometer 32 on the basis of measurements with a pressure indicator 34 connected to a pressure sensor which is not shown for detecting the internal pressure of the piping 100 and with the correction potentiometer 33. The pressure sensor and the pressure indicator 34 form a piping pressure measurement means in this embodiment and the piping pressure measuring means, the correction electric potential difference measuring electrodes 12g and 12h, the correction potentiometer 33, and the correction arithmetic unit 35 form an intra-crack electric potential difference correction means in this embodiment.

Furthermore, the centralized control room 30 contains a crack length calculating unit 36 which is a crack length calculation means for calculating a length of the crack 100b in the piping 100 on the basis of the electric potential difference corrected by the correction arithmetic unit 35.

The crack monitoring method with this crack monitoring apparatus will be described below.

[Specifying Crack Position]

In a weld 100a or the like in a high-temperature thick-walled piping 100 (for example, a main steam pipe (Thickness: Approx. 100 mm) or a high-temperature reheat steam pipe (Thickness: Approx. 30 to 40 mm)) of a boiler of a plant such as a power station, the presence or absence of a crack 100b and its length are checked by using a nondestructive inspection method (TOFD method etc.) which has been conventionally used for periodic inspections.

[Electrode Attachment Process]

After ascertaining the position and the length of the crack 100b, the sensor head 10 is fixed in a regulated position to the outer circumferential surface of the high-temperature thick-walled piping 100. This regulated position is a place where an electric resistance (an electric potential difference) can be measured most sensitively at a growth of the crack 100b. It is selected after an electric field analysis with a computer for an electric potential distribution around the crack 100b. Because the amount of voltage change caused by the growth of the crack 100b is extremely small ($10^{-3}$ to $10^{-5}$ V), the measuring process requires high precision.

According to the electric field analysis apparatus, as shown in FIG. 4, it is preferable to attach the sensor head 10 to the high-temperature thick-walled piping 100 in such a way that the crack 100b on the center side is generally centered between the crack electric potential difference measuring electrodes 12c and 12d and in a direction (a crosswise direction) perpendicular to the direction of likely growth (a lengthwise direction) of the crack 100b and that the crack 100b on the tip side thereof in the growing direction is centered between the crack electric potential difference measuring electrodes 12e and 12f in a direction (a crosswise direction) perpendicular to the direction of likely growth (a lengthwise direction) of the crack 100b. Particularly, if a length L between the current input-output electrodes 12a and 12b is approximately 3.5 or greater times as long as a thickness of the high-temperature thick-walled piping 100, the electric potential distribution around the crack 100b is uniform, therefore, for high-temperature thick-walled piping 100 having a thickness of approximately 30 to 40 mm, it is preferable to set the length L between the current input-output electrodes 12a and 12b to approximately 150 mm.

Figure 6:
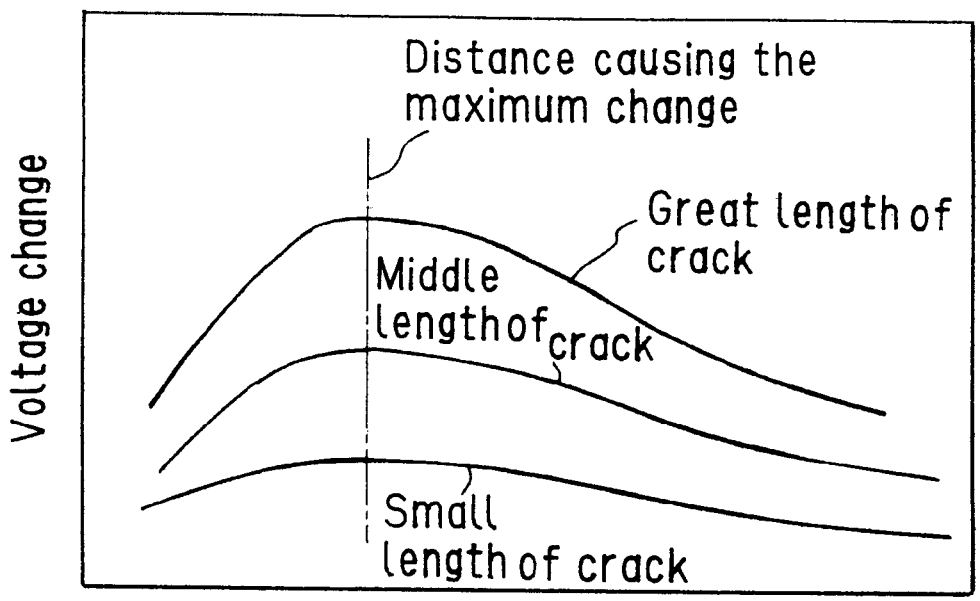
FIG. 6 is a graph representing the relationship between the distance between the power input-output electrodes and the voltage change for each length of a crack.

In addition, as shown in FIG. 6, by obtaining a relationship between a length W between the crack electric potential difference measuring electrodes 12c and 12d and between the crack electric potential difference measuring electrodes 12e and 12f and the voltage change for each length of the crack 100b, the length W which causes the maximum voltage change may be determined by referring to FIG. 6 and is independent of the length of the crack 100b.

Accordingly, since the thickness of the high-temperature thick-walled piping 100 and the length of the crack 100b are generally within a predictable range, therefore, even when the positional relationships between the electrodes 12a to 12h, such as the length L between the current input-output electrodes 12a and 12b and the length W between the crack electric potential difference measuring electrodes 12c and 12d are fixed, the optimal condition can be obtained at all times. Therefore, if the sensor head 10 is attached to the high-temperature thick-walled piping 100 in such a way that the crack 100b is placed in a regulated position of the protective box 11 by positioning and fixing the electrodes 12a to 12h to the protective box 11 so as to satisfy the above various conditions, the electrodes 12a to 12h can be easily mounted in the regulated positions.

Figure 7:
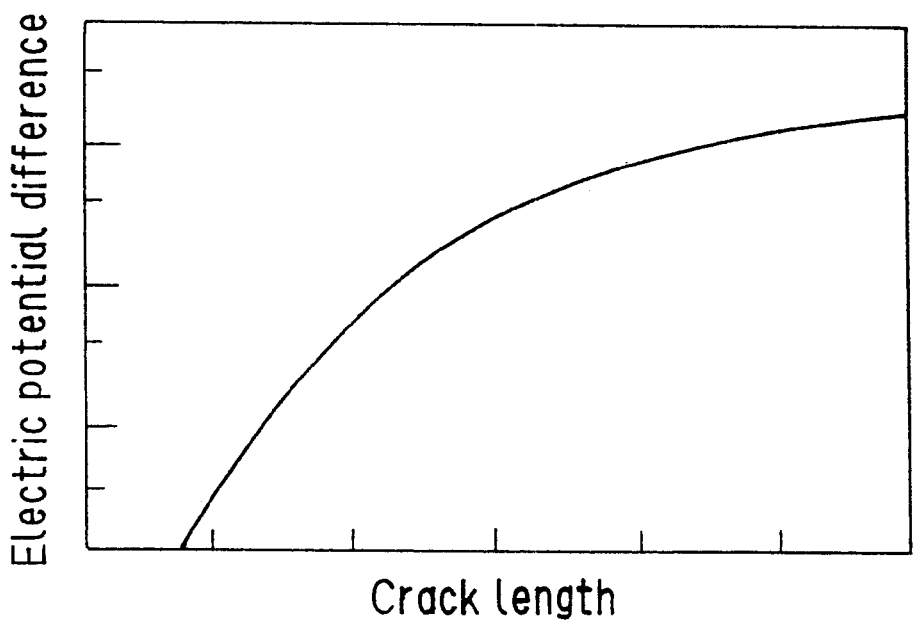
FIG. 7 is a graph representing the relationship between the length of a crack and the electric potential difference.

Furthermore, as shown in FIG. 7, it should be noted that it is necessary to previously obtain a crack growth evaluation line indicating a relationship between the length of the crack 100b and the electric potential difference in the crack 100b.

[Intra-crack Electric Potential Difference Measurement Process]

After attaching the sensor head 10 and starting the operation of the plant for a periodic inspection as described above, alternating current is supplied between the current input-output electrodes 12a and 12b from the alternating power supply 31 in an alternating current resistance method to measure electric potential differences between the crack electric potential difference measuring electrodes 12c and 12d and between the crack electric potential difference measuring electrodes 12e and 12f with the crack potentiometer 32.

Simultaneously, the electric potential difference between the correction electric potential difference measuring electrodes 12g and 12h is measured by using the correction potentiometer 33 and the internal pressure of the high-temperature thick-walled piping 100 is measured by using the pressure indicator 34 from the pressure sensor.

If the frequency of the current applied to the electrodes 12a and 12b is higher than 10 Hz at this point, an electric resistance can be measured only on the surface of the high-temperature thick-walled piping 100. Therefore, to measure the crack 100b inside the high-temperature thick-walled piping 100, it is necessary to apply alternating current of a 10 Hz or lower frequency. This alternating current resistance method facilitates noise processing; therefore, it is very convenient to check for even a small change in the crack 100b.

[Intra-crack Electric Potential Difference Correction Process]

Figure 8:
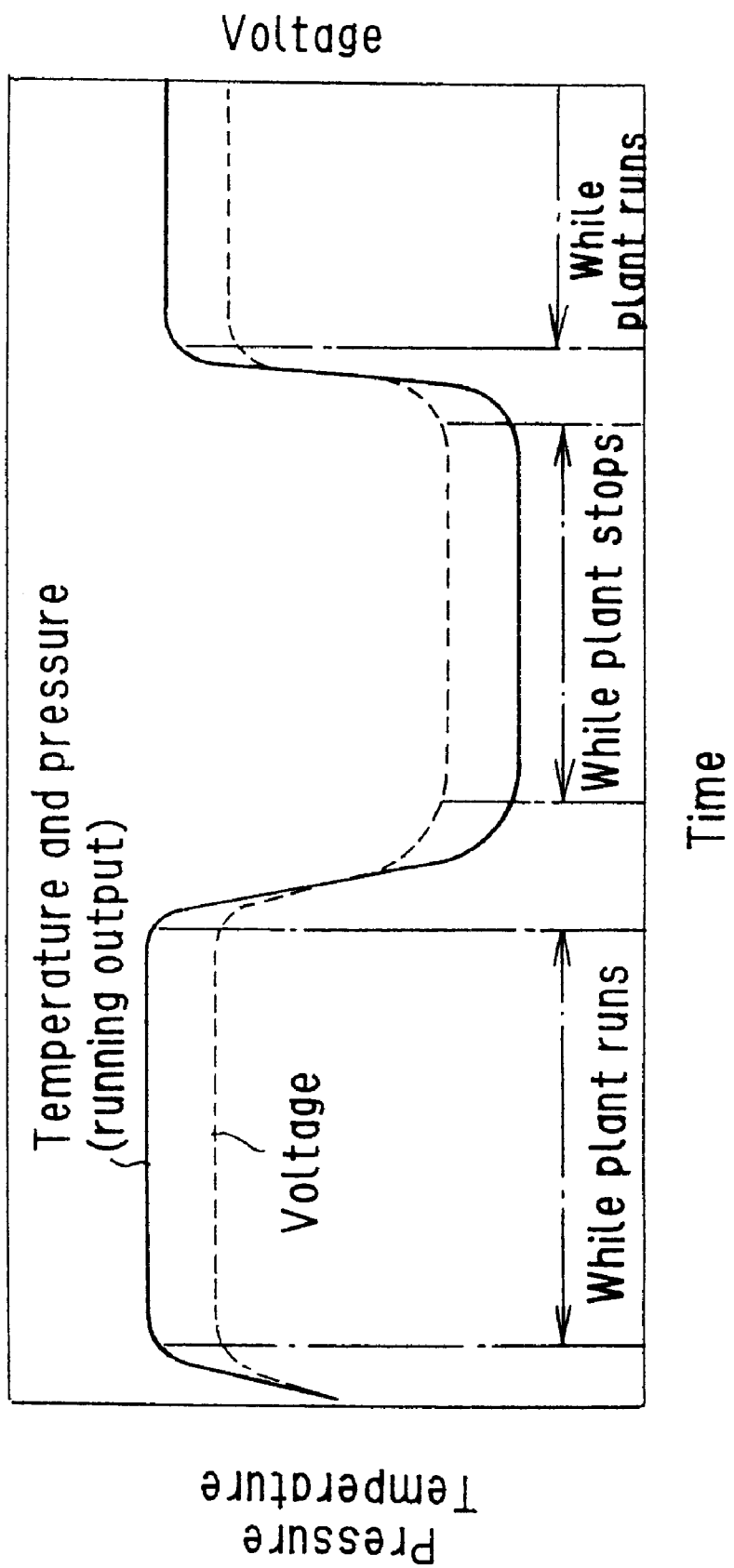
FIG. 8 is a graph representing changes in voltages in a crack and plant running outputs relative to time.

FIG. 8 shows the changes voltage associated with the pipe portion containing the crack 100b, the temperature and pressure of the high-temperature thick-walled piping 100, and the operation of the plant, relative to time measured, as described above. As is apparent from FIG. 8, the voltage detected is high while the plant is operating at high temperature and pressure of the high-temperature within the thick-walled piping 100 and is low while the plant stops with temperature and pressure in the high-temperature thick-walled piping 100.

In other words, the electric resistance of the high-temperature thick-walled piping 100 itself changes as a function of a temperature change within the piping and the size of the crack 100b also changes as a function of a pressure change, by which the voltage also changes.

Therefore, an error caused by a temperature factor is removed by correcting the electric potential differences between the crack electric potential difference measuring electrodes 12c and 12d and between the crack electric potential difference measuring electrodes 12e and 12f by using the correction arithmetic unit 35 on the basis of the electric potential difference between the correction electric potential difference measuring electrodes 12g and 12h and the electric potential differences between the crack electric potential difference measuring electrodes 12c and 12d and between the crack electric potential difference measuring electrodes 12e and 12f are corrected for each corresponding pressure by using the correction arithmetic unit 35 on the basis of a result of the measurement with the pressure indicator 34.

Figure 9:
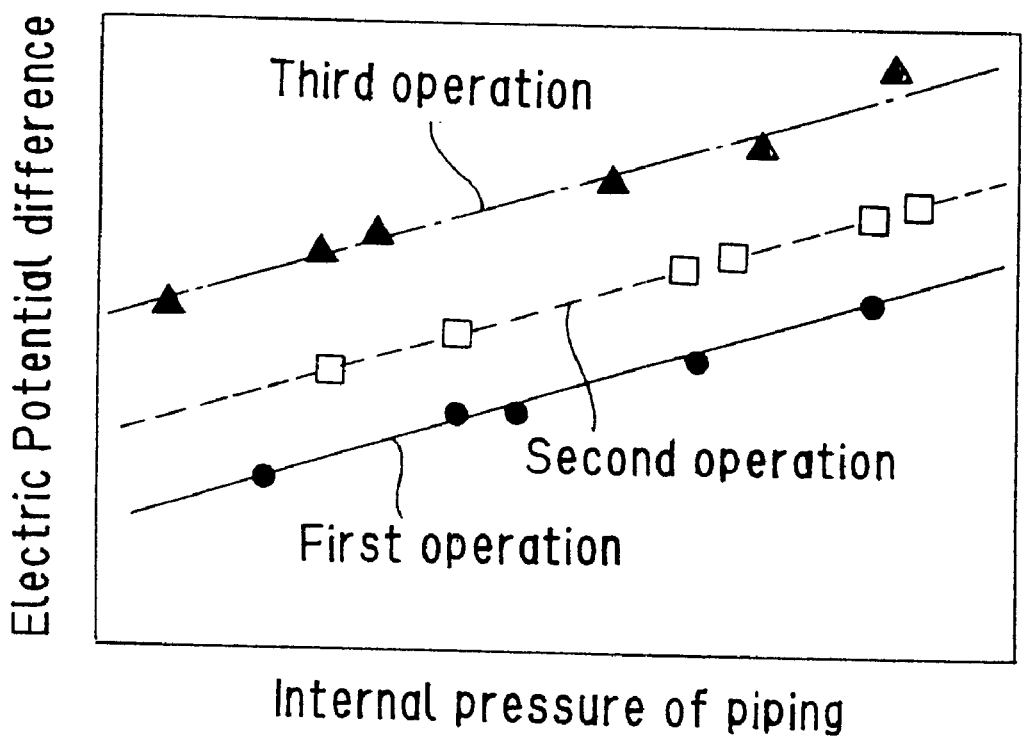
FIG. 9 is a graph representing the relationship between the electric potential difference in a crack and the internal pressure in the piping.

Referring to FIG. 9, there is shown a relationship between the electric potential difference in the crack 100b corrected in this manner and the internal pressure of the high-temperature thick-walled piping 100. As is apparent from FIG. 9, a correlation with the pressure for each plant operation time is obtained and the electric potential difference in the crack 100b is increased if the crack 100b grows with the continued operation of the plant.

[Crack Length Calculation Process]

Figure 10:
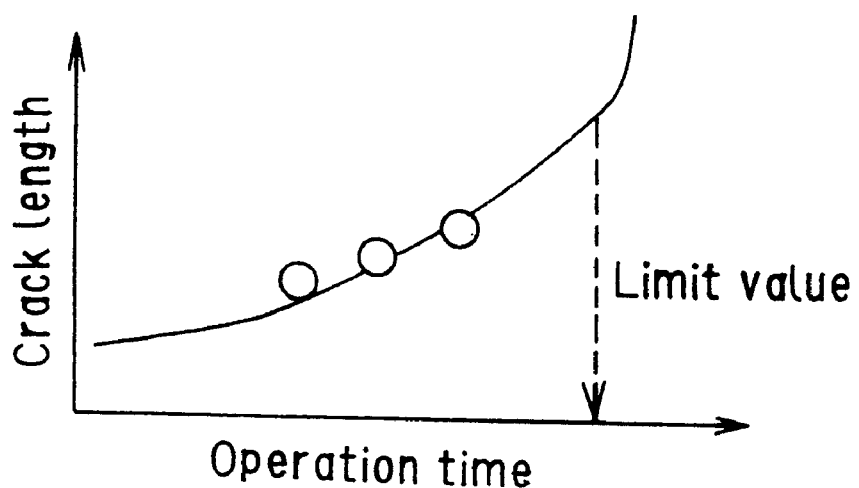
FIG. 10 is a graph representing the relationship between the operation time of a plant and the length of a crack.

Subsequently, the crack Length Calculating unit 36 calculates the length of the crack 100b on the basis of the crack growth evaluation line (FIG. 7) described above from the electric potential difference in the crack 100b corrected by the correction arithmetic unit 35. A limit value is obtained by plotting this length for each plant operation time as shown in FIG. 10.

Therefore, according to the foregoing crack monitoring method and crack monitoring apparatus, the length of the crack 100b can be monitored even while the plant runs. Thus, it is possible to improve accuracy and safety significantly in comparison with the conventional means whereby only a prediction based on a result of the periodic inspection is available.

In addition, by providing a plurality of sensor heads 10, attaching these sensor heads 10 to circumferential portions of respective high-temperature thick-walled piping portions 100 about the cracks 100b, and connecting the sensor heads 10 to the potentiometers 32 and 33 in the centralized control room 30 via the repeater 24 or the like, electric potential differences between the electrodes 12c to 12h of the sensor heads 10 are measured by using the potentiometers 32 and 33. The results of the measurements are corrected for the respective sensor heads 10 by using the correction arithmetic unit 35. The lengths of the cracks 100b adjacent to the sensor heads 10 are then calculated by the crack length calculating unit 36 on the basis of the electric potential differences for the sensor heads 10 obtained by the correction arithmetic unit 35, by which the plurality of the cracks 100b on the plurality of the high-temperature thick-walled piping portions 100 can be collectively monitored easily at any time.

While the crack on the center side is put between one pair of crack electric potential difference measuring electrodes 12c and 12d and the crack 100b on the tip side thereof in its direction. of likely growth is put between the other pair of crack electric potential difference measuring electrodes 12e and 12f so that the growth of the crack 100b can be grasped more accurately in this embodiment. The length of the crack 100b can be monitored by using only a pair of crack electric potential difference measuring electrodes 12c and 12d.

While alternating current at a frequency of 10 Hz or less is supplied between the current input-output electrodes 12a and 12b of the sensor head 10 from the alternating current power supply 31 to monitor the crack 100b inside the high-temperature thick-walled piping 100 in this embodiment, alternating current at a frequency of 50 Hz or higher can be supplied between the current input-output electrodes 12a and 12b of the sensor head 10 from the alternating power supply 31, for example, to monitor the material deterioration status on the surface of the high-temperature thick-walled piping 100 caused by a creep void or the like. Furthermore, 10 Hz or lower alternating current and 50 Hz or higher alternating current can be supplied alternately to monitor the crack 100b inside the high-temperature thick-walled piping 100 simultaneously with monitoring the material deterioration status on the surface of the high-temperature thick-walled piping 100 caused by a creep void or the like, thereby improving safety of the plant.

While an error caused by a temperature factor is removed by correcting the electric potential differences between the crack electric potential difference measuring electrodes 12c and 12d and between the crack electric potential difference measuring electrodes 12e and 12f on the basis of the electric potential difference between the correction electric potential difference measuring electrodes 12g and 12h in this embodiment, it is also possible to remove any error caused by a temperature factor by previously obtaining a correlation between the temperature of the high-temperature thick-walled piping 100 and the electric potential difference, attaching a heat-resistant temperature sensor such as a thermocouple to the high-temperature thick-walled piping 100, and correcting the electric potential differences in the crack 100b on the basis of the temperature measured by the temperature sensor, for example, instead of using the correction electric potential difference measuring electrodes 12g and 12h or the correction potentiometer 33. Furthermore, more accurate measurements can be obtained by using both of these methods. In the above embodiment, a piping temperature measurement means is formed by the temperature sensor or the like.

While the correction arithmetic unit 35 is used to correct the electric potential differences between the crack electric potential difference measuring electrodes 12c and 12d and between the crack electric potential difference measuring electrodes 12e and 12f for each corresponding pressure on the basis of the measurement results of the pressure indicator 34 in this embodiment, it can be omitted if a pressure fluctuation is relatively small.

Second Embodiment

A description will be given below for a second embodiment of a crack monitoring method and a crack monitoring apparatus according to this embodiment.

The crack monitoring apparatus according to this embodiment is the same as one for the first embodiment described above except for the following:

(1) A thermocouple for measuring the temperature of high-temperature thick-walled piping 100 is arranged in the sensor head 10.
(2) The thermocouple and a pressure indicator 34 are electrically connected to a crack length calculating unit 36 in a centralized control room 30.

Next, a crack monitoring method with this crack monitoring apparatus will be described below.
[Specifying Crack Position]
The crack position specifying process is the same as one for the first embodiment described above.
[Electrode Attachment Process]
The electrode attachment process is the same as one for the first embodiment described above.

It should be noted that, however, this process does not require any crack growth evaluation line indicating a relationship between the length of a crack 100b and the electric potential difference in the crack 100b.
[Intra-crack Electric Potential Difference Measurement Process]
The intra-crack electric potential difference measurement process is the same as one for the first embodiment described above.

It should be noted that, however, it is required to measure the temperature of high-temperature thick-walled piping 100 by using the thermocouple.
[Intra-crack Electric Potential Difference Correction Process]
The intra-crack electric potential difference correction process is the same as one for the first embodiment described above.

It should be noted that, however, the correction is not performed according to the pressure as described above.

Figure 11:
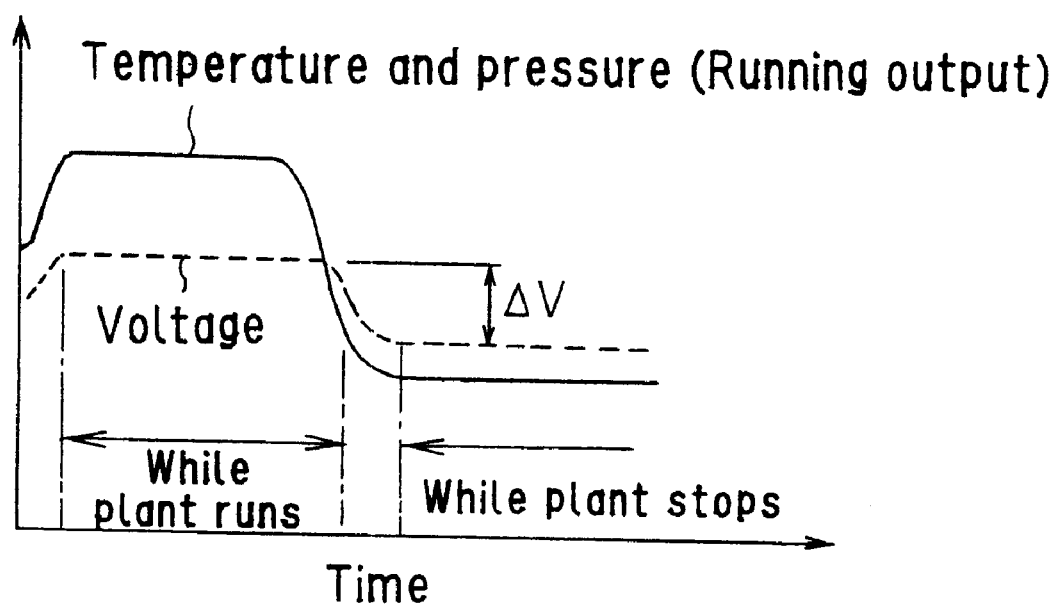
FIG. 11 is a graph representing changes in voltages in a crack and plant running outputs relative to time.

[Crack Length Calculation Process]
Referring to FIG. 11, there is shown the change in voltage of the crack 100b portion and the operation of a plant (the temperature and pressure of the high-temperature thick-walled piping 100) relative to time. As is apparent from FIG. 11, the voltage is increased while the plant runs (at high temperature and pressure within the high-temperature thick-walled piping 100) and is decreased while the plant is stopped (at low temperature and pressure within the high-temperature thick-walled piping 100).

In other words, the electric resistance of the high-temperature thick-walled piping 100 itself changes together with the temperature and the size of the crack 100b changes together with the pressure, by which the voltage also changes.

At this point, the voltage change caused by the pressure fluctuation is described below in further detail.

If the pressure inside the high-temperature thick-walled piping 100 is high, as during the operation of a plant, a large stress $\sigma_1$ is applied to the high-temperature thick-walled piping 100 to make a long width (an opening amount) $\sigma_1$ of the crack 100b. On the other hand, if the pressure inside the high-temperature thick-walled piping 100 is low, as during a stoppage of the plant, a small stress $\sigma_2$ is applied to the high-temperature thick-walled piping 100 to make a short width (an opening amount) $\sigma_2$ of the crack 100b.

Considering the above on a plane surface, there is a relationship between the stress and the opening amount as represented by the following formulas (1) and (2):

$$\sigma_1 = (4\sigma_1 a/E^-)V_1(a/b) \qquad (1)$$

$$\sigma_2 = (4\sigma_2 a/E^-)V_1(a/b) \qquad (2)$$

where a is a half value of the length of the crack 100b, b is a half value of the length (infinity) in the lengthwise direction of the crack 100b on the plane, $E^-$ is a Young's modulus, and $V_1$ is a correction coefficient.

The above formula (1) minus the formula (2) is the following formula (3):

$$\sigma_1 - \sigma_2 = (\sigma_1 - \sigma_2)(4a/E^-)V_1(a/b)\Delta\sigma = \Delta\sigma(4a/E^-)V_1(a/b) \qquad (3)$$

In the above formula, a change $\Delta\sigma$ of the opening amount of the crack 100b is almost equal to the change of the cross-sectional area of the crack 100b and the change of the cross-sectional area has a proportional relationship with the electric potential difference change $\Delta V$ in the crack 100b, by which the length 2a of the crack 100b is obtained from the above formula (3) by calculating $\Delta\sigma$ from $\Delta V$ and a stress change $\Delta\sigma$ from the temperature and the internal pressure of the high-temperature thick-walled piping 100.

Specifically, the crack length calculating unit 36 performs arithmetic operations based on the steps as described below.
[First Step]
A correlation is obtained between the maximum crack length 2 of the crack 100b for each stress change $\Delta\sigma$ and the electric potential change $\Delta V$ in the crack 100b on the basis of an electric field analysis of the welded portion of the piping surrounding the crack 100b in the high-temperature thick-walled piping 100 or experiments.
[Second Step]
A stress change $\Delta\sigma$ is obtained between two points in time, that is, the time when a high load is applied and the time when a low load is applied in the piping 100 on the basis of the temperature of the high-temperature thick-walled piping 100 measured by the thermocouple and the internal pressure of the high-temperature thick-walled piping 100 measured by the pressure indicator 34.

[Third Step]

The length $2a$ of the crack 100b corresponding to the stress change $\Delta\sigma$ is obtained from the electric potential change $\Delta V$ between the two points in time.

Figure 12:
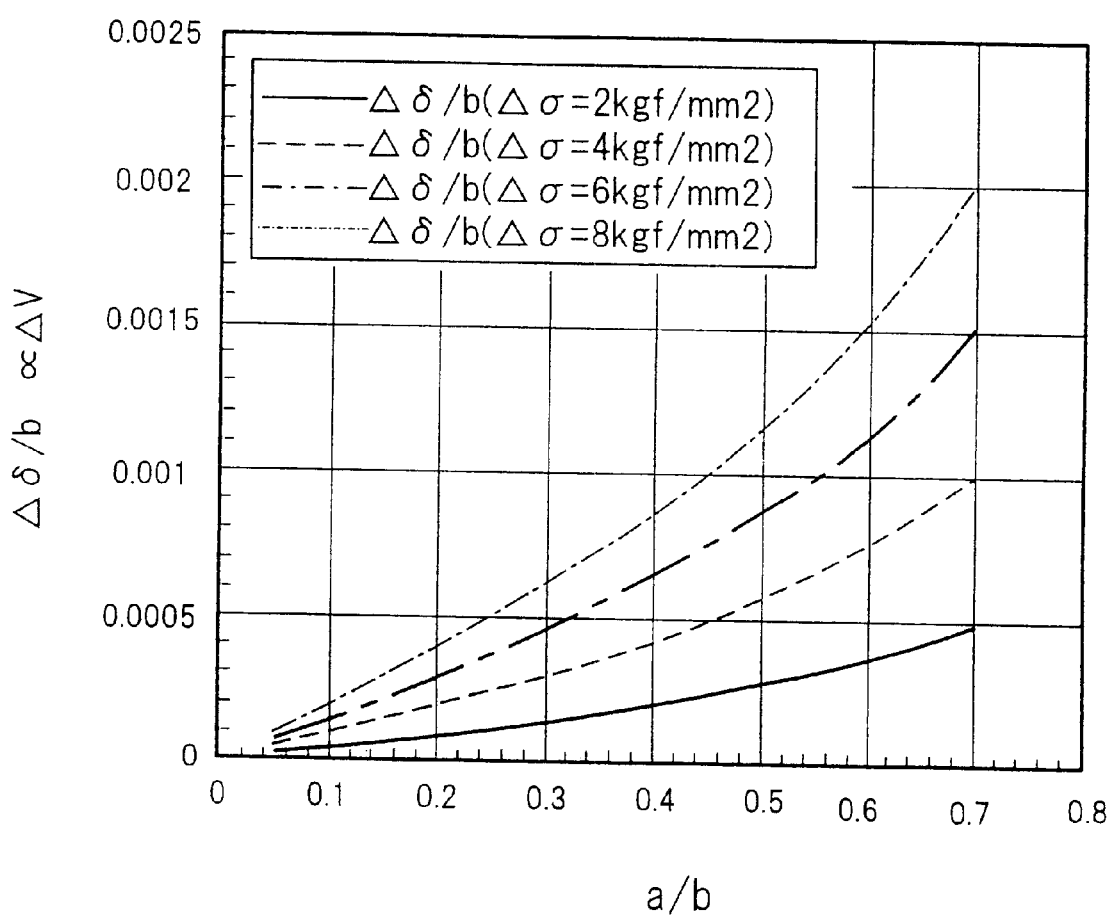
FIG. 12 is a graph representing the relationship between the amount change in the opening of a crack for each change in stress and the half value of the length of the crack.

In other words, there is a correlation between the change in the crack opening $\Delta\sigma$ and the half value a of the length of the crack 100b for each stress change $\Delta\sigma$ as is shown in FIG. 12 and therefore the length $2a$ of the crack 100b is obtained on the basis of the correlation.

Therefore, according to the crack monitoring method and the crack monitoring apparatus, it is possible to measure the crack in a shorter time in comparison with the first embodiment. described above as well as achieving the same effects as in the first embodiment.

In addition, by combining the method and apparatus with the first embodiment, the length of the crack 100b can be measured more precisely.

While the stress $\sigma$ applied to the piping 100 is obtained on the basis of the temperature of the high-temperature thick-walled piping 100 measured by the thermocouple and the internal pressure on the high-temperature thick-walled piping 100 measured by the pressure indicator 34 in this embodiment, it is also possible to attach a stress sensor or the like to the inside of the sensor head 10 instead of the thermocouple or the pressure indicator to measure the stress of the surrounding portion of the crack 100b of the high-temperature thick-walled piping 100 and to send the result to the crack length calculating unit 36.

A crack monitoring method for monitoring a crack inside piping according to a first aspect of the invention comprises attaching a pair of heat-resistant current input-output electrodes to an outer circumferential surface of the piping such that the crack whose position is previously specified is put between the pair of heat-resistant current input-output electrodes and attaching at least one pair of heat-resistant crack electric potential difference measuring electrodes to the outer circumferential surface of the piping such that they are put between the current input-output electrodes, supplying an alternating current between the current input-output electrodes and measuring an electric potential difference between the crack electric potential difference measuring electrodes, correcting the electric potential difference between the crack electric potential difference measuring electrodes, and calculating the length of the crack on the basis of the electric potential difference obtained by the intra-crack electric potential difference correction process, whereby the length of the crack can be monitored even if the piping is at a high temperature during normal plant operation. Therefore, the accuracy and safety is significantly improved in comparison with the conventional monitoring methods which provide only a prediction of crack growth from a periodic inspection.

A crack monitoring method according to a second aspect of the invention is one according to the first aspect of the invention, wherein the attached positions of the current input-output electrodes and the crack electric potential difference measuring electrodes are set on the basis of an electric field analysis of the welded portion. of the piping surrounding the crack so that the electric potential difference can be measured most sensitively at a growth of the crack on the piping, whereby the electric potential difference can be measured at a high precision even if the difference is very small when caused by the growth of the crack.

A crack monitoring method according to a third aspect of the invention is one according to the second aspect of the invention, wherein a pair of crack electric potential difference measuring electrodes are attached to the piping such that the crack on the center side is put between the electrodes in a direction perpendicular to the direction of likely growth of the crack in the piping, whereby the electric potential difference can be measured at a high precision even if the difference is very small when caused by the growth of the crack.

A crack monitoring method according to a fourth aspect of the invention is one according to the third aspect of the invention, wherein the other pair of crack electric potential difference measuring electrodes are attached to the piping in the electrode attachment process such that the crack on the tip side thereof in the direction of likely growth is put between the electrodes in the direction perpendicular to the direction of likely growth of the crack in the piping, whereby a growth of the crack can be determined more accurately.

A crack monitoring method according to a fifth aspect of the invention is one according to the first aspect of the invention, wherein the current input-output electrodes and the crack electric potential difference measuring electrodes are removably attached to the outer circumferential surface of the piping in the electrode attachment process, whereby the electrodes can be easily removed.

A crack monitoring method according to a sixth aspect of the invention is one according to the first aspect of the invention, wherein an alternating current of a frequency of 10 Hz or less is supplied between the current input-output electrodes in the intra-crack electric potential difference measurement process, whereby the crack in the piping can be measured reliably.

A crack monitoring method according to a seventh aspect of the invention is one according to the first aspect of the invention, wherein an alternating current of a frequency of 50 Hz or greater is supplied between the current input-output electrodes in the intra-crack electric potential difference measurement process, whereby it is also possible to monitor material deterioration conditions and the like caused by creep void on the surface of the piping.

A crack monitoring method according to an eighth aspect of the invention is one according to the first aspect of the invention, wherein an alternating current of a frequency alternating between 10 Hz or less and 50 Hz or higher is supplied between the current input-output electrodes in the intra-crack electric potential difference measurement process, whereby it is also possible to monitor material deterioration conditions and the like caused by creep void on the surface of the piping. It improves the safety further.

A crack monitoring method according to a ninth aspect of the invention is one according to the first aspect of the invention, wherein the intra-crack electric potential difference correction process is used to correct the electric potential difference between the crack electric potential difference measuring electrodes on the basis of the electric potential difference between the pair of heat-resistant correction electric potential difference measuring electrodes attached to the outer circumferential surface of the piping, whereby the electric potential difference between the crack electric potential difference measuring electrodes can be corrected accurately.

A crack monitoring method according to a tenth aspect of the invention is one according to the first aspect of the invention, wherein the intra-crack electric potential difference correction process is used to correct the electric potential difference between the crack electric potential difference measuring electrodes on the basis of the temperature of the piping, whereby the electric potential difference between the crack electric potential difference measuring electrodes can be corrected accurately.

A crack monitoring method according to an 11th aspect of the invention is one according to the first aspect of the invention, wherein the intra-crack electric potential difference correction process is used to correct the electric potential difference between the crack electric potential difference measuring electrodes on the basis of the internal pressure of the piping, whereby the electric potential difference between the crack electric potential difference measuring electrodes can be. corrected accurately.

A crack monitoring method according to a 12th aspect of the invention is one according to the first aspect of the invention, wherein the crack length calculation process is used to calculate the length of the crack from the electric potential difference obtained by the intra-crack electric potential difference correction process on the basis of a correlation between the length of the crack obtained from an electric field analysis of a surrounding portion of the crack on the piping or experimentally and the electric potential difference in the crack, whereby the length of the crack can be obtained accurately.

A crack monitoring method according to a 13th aspect of the invention is one according to the first aspect of the invention, wherein the crack length calculation process further comprises a first step of obtaining a correlation between the maximum crack length of the crack for each stress change and an electric potential difference change in the crack on the basis of the electric field analysis of the welded portion of the piping surrounding the crack in the piping or experimentally, a second step of obtaining a stress change between two points in time, that is, the time when a high load is applied and the time when a low load is applied in the piping on the basis of the temperature and the internal pressure of the piping, and a third step of obtaining a length $2a$ of the crack corresponding to the stress change from the electric potential difference change between the above two points in time, whereby the length of the crack can be obtained accurately.

On the other hand, a crack monitoring apparatus according to a 14th aspect of the invention to solve the above problem is a crack monitoring apparatus for monitoring a crack generated inside the piping, comprising a pair of current input-output electrodes made of heat-resistant material attached to an outer circumferential surface of the piping, a sensor head having at least one pair of crack electric potential difference measuring electrodes made of heat-resistant material attached to the outer circumferential surface of the piping such that they are put between the current input-output electrodes, an electric alternating current power supply for supplying an alternating current between the current input-output electrodes of the sensor head, a crack electric potential difference measurement means for measuring an electric potential difference between the crack electric potential difference measuring electrodes of the sensor head, an intra-crack electric potential difference correction means for correcting the electric potential difference between the crack electric potential difference measuring electrodes of the sensor head measured by the crack electric potential difference measurement means, and a crack length calculation means for calculating the length of the crack on the basis of the electric potential difference obtained by the intra-crack electric potential difference correction means, whereby the length of the crack can be monitored even if the piping is at a high temperature during operation of a plant. Therefore, it is possible to improve the accuracy and the safety significantly in comparison with the conventional monitoring which provides only a prediction resulting from a periodic inspection.

A crack monitoring apparatus according to a 15th aspect of the invention is one according to the 14th aspect of the invention, wherein the positions of the current input-output electrodes and those of the crack electric potential difference measuring electrodes of the sensor head are set on the basis of an electric field analysis of the welded portion of the piping surrounding the crack in the piping so that the electric potential difference can be measured most sensitively at the growth of the crack in the piping, whereby the electric potential difference can be measured at a high precision even if the difference is very small when caused by the growth of the crack.

A crack monitoring apparatus according to a 16th aspect of the invention is one according to the 15th aspect of the invention, wherein the pair of crack electric potential difference measuring electrodes of the sensor head are attached to the piping such that the crack on the center side is put between the electrodes in a direction perpendicular to the direction of likely growth of the crack in the piping, whereby the electric potential difference can be measured at a high precision even if the difference is very small when caused by the growth of the crack.

A crack monitoring apparatus according to a 17th aspect of the invention is one according to the 16th aspect of the invention, wherein the other pair of crack electric potential difference measuring electrodes of the sensor head are attached to the piping such that the crack on the tip side thereof in the direction of likely growth is put between the electrodes in a direction perpendicular to the direction of likely growth of the crack in the piping, whereby the growth of the crack can be determined more accurately.

A crack monitoring apparatus according to a 18th aspect of the invention is one according to the 14th aspect of the invention, wherein there is provided an attachment means for removably attaching the sensor head to the outer circumferential surface of the piping, whereby the sensor head can be attached or detached easily.

A crack monitoring apparatus according to a 19th aspect of the invention is one according to the 14th aspect of the invention, wherein an alternating current of a frequency of 10 Hz or less is supplied by the alternating current power supply, whereby the crack inside the piping can be measured reliably.

A crack monitoring apparatus according to a 20th aspect of the invention is one according to the 14th aspect of the invention, wherein an alternating current of a frequency of 50 Hz or greater is supplied by the alternating current power supply, whereby it is possible to monitor material deterioration or other conditions caused by a creep void or the like on the surface of the piping.

A crack monitoring apparatus according to a 21st aspect of the invention is one according to the 14th aspect of the invention, wherein an alternating current of a frequency alternating between 10 Hz or less and 50 Hz or higher one is supplied by the alternating current power supply, whereby it is possible to monitor the crack inside the piping while monitoring the material deterioration or other conditions caused by a creep void or the like on the surface of the piping. Therefore, the safety can be further improved.

A crack monitoring apparatus according to a 22nd aspect of the invention is one according to the 14th aspect of the invention, wherein the intra-crack electric potential difference correction means comprises a pair of correction electric potential difference measuring electrodes made of heat-resistant material arranged in the sensor head so as to be attached to the outer circumferential surface of the piping and the correction electric potential difference measurement means for measuring an electric potential difference between the correction electric potential difference measuring electrodes, whereby the electric potential difference between the crack electric potential difference measuring electrodes can be corrected accurately.

A crack monitoring apparatus according to a 23rd aspect of the invention is one according to the 14th aspect of the invention, wherein the intra-crack electric potential difference correction means comprises a piping temperature measurement means for measuring the temperature of the piping, whereby the electric potential difference between the crack electric potential difference measuring electrodes can be corrected accurately.

A crack monitoring apparatus according to a 24th aspect of the invention is one according to the 14th aspect of the invention, wherein the intra-crack electric potential difference correction means comprises a piping pressure measurement means for measuring the internal pressure of the piping, whereby the electric potential difference between the crack electric potential measuring electrodes can be corrected accurately.

A crack monitoring apparatus according to a 25th aspect of the invention is one according to the 14th aspect of the invention, wherein the crack length calculation means calculate the length of the crack from the electric potential difference obtained by the intra-crack electric potential difference correction means on the basis of a correlation between the length of the crack obtained from an electric field analysis of the welded portion of the piping surrounding the crack in the piping or experimentally and the electric potential difference in the crack, whereby the length of the crack can be obtained accurately.

A crack monitoring apparatus according to a 26th aspect of the invention is one according to the 14th aspect of the invention, wherein the crack length calculation means performs a first step of obtaining a correlation between the maximum crack length of the crack for each stress change and an electric potential difference change in the crack on the basis of the electric field analysis of the welded portion surrounding the crack in the piping or experimentally, a second step of obtaining a stress change between two points in time, that is, the time when a high load is applied and the time when a low load is applied within the piping on the basis of the temperature and the internal pressure of the piping, and a third step of obtaining the length of the crack corresponding to the stress change from the electric potential difference change between the above two points in time, whereby the length of the crack can be obtained accurately.

A crack monitoring apparatus according to a 27th aspect of the invention is one according to the 14th aspect of the invention, wherein a plurality of sensor heads are arranged, the intra-crack electric potential difference measurement means measures electric potential differences between the crack electric potential difference measuring electrodes of each of the plurality of the sensor heads, the intra-crack electric potential difference correction means corrects the electric potential differences between the crack electric potential difference measuring electrodes of the plurality of sensor heads measured by the crack electric potential difference measurement means, and the crack length calculation means calculates the lengths of the cracks on the basis of the electric potential differences obtained by the intra-crack electric potential difference correction means, whereby the plurality of cracks on the plurality of the piping portions can be easily monitored collectively at a time.

A crack monitoring apparatus according to a 28th aspect of the invention is one according to the 14th aspect of the invention, wherein the intra-crack electric potential difference measurement means, the intra-crack electric potential difference correction means, and the crack length calculation means are arranged in a remote area far from the piping, whereby a crack can be monitored from an area far from the piping.

What is claimed is:

1. A method for monitoring a crack that is generated within a welded portion of a high temperature, thick-walled piping of a plant, which method is accomplished during the operation of the plant, comprising:

attaching a pair of heat-resistant current input-output electrodes to an outer circumferential surface of the welded portion of the piping such that the crack whose position is previously specified is put between the pair of heat-resistant current input-output electrodes;

attaching at least one pair of heat-resistant crack electric potential difference measuring electrodes to the outer circumferential surface of the piping such that they are put between the current input-output electrodes;

alternately supplying an alternating current of a frequency of either 10 Hz or lower or 50 Hz or higher between said current input-output electrodes;

measuring an electric potential difference between said crack electric potential difference measuring electrodes;

correcting the electric potential difference between said crack electric potential difference measuring electrodes;

protecting the heat resistant current input-output electrodes and the electric potential difference measuring electrodes by enclosing those electrodes in a protective box; and calculating the length of the crack on the basis of said electric potential difference obtained by said intra-crack electric potential difference correction process.

2. A crack monitoring method according to claim 1, wherein the attached positions of said current input-output electrodes and said crack electric potential difference measuring electrodes are set on the basis of an electric field analysis of the portion of the welded portion of the piping surrounding the crack so that the electric potential difference can be measured most sensitively at a growth of the crack in said piping.

3. A crack monitoring method according to claim 2, wherein a pair of said crack electric potential difference measuring electrodes are attached to the piping such that the crack on the center side is put between the electrodes in a direction perpendicular to the direction of likely growth of said crack in said piping.

4. A crack monitoring method according to claim 3, wherein the other pair of said crack electric potential difference measuring electrodes are attached to the piping such that the crack on the tip side thereof in the direction of likely growth is put between the electrodes in a direction perpendicular to the direction of likely growth of said crack in said piping.

5. A crack monitoring method according to claim 1, wherein said current input-output electrodes and said crack electric potential difference measuring electrodes are removably attached to the outer circumferential surface of said piping.

6. A crack monitoring method according to claim 1, wherein said intra-crack electric potential difference correction is used to correct the electric potential difference between said crack electric potential difference measuring electrodes on the basis of the electric potential difference between the pair of heat-resistant correction electric potential difference measuring electrodes attached to the outer circumferential surface of said piping.

7. A crack monitoring method according to claim 1, wherein said intra-crack electric potential difference correction is used to correct said electric potential difference between said crack electric potential difference measuring electrodes on the basis of the temperature of said piping.

8. A crack monitoring method according to claim 1, wherein said intra-crack electric potential difference correction is used to correct said electric potential difference between said crack electric potential difference measuring electrodes on the basis of the internal pressure of said piping.

9. A crack monitoring method according to claim 1, wherein said crack length calculation is used to calculate the length of the crack from said electric potential difference obtained by said intra-crack electric potential difference correction on the basis of a correlation between the length of the crack obtained from an electric field analysis of the portion of the welded portion of the piping surrounding said crack in said piping or from an experiment and the electric potential difference in the crack.

10. A crack monitoring method according to claim 1, wherein said crack length calculation comprises:
    obtaining a correlation between the maximum crack length of said crack for each stress change and an electric potential difference change in the crack on the basis of the electric field analysis of the portion of the welded portion surrounding said crack in said piping or experimentally;
    obtaining a stress change between two points of time, that is, the time when a high load is applied on said piping and the time when a low load is applied on said piping, said load being determined on the basis of the temperature and internal pressure of said piping; and
    obtaining the length of said crack corresponding to the stress change from the electric potential difference change between the two points of time.

11. An apparatus for monitoring a crack that is generated within a welded portion of a high temperature, thick-walled piping of a plant during the operation of the plant comprising:
    a pair of current input-output electrodes made of heat-resistant material attached to an outer circumferential surface of the welded portion of the piping;
    a sensor head having at least one pair of crack electric potential difference measuring electrodes made of a heat-resistant material attached to the outer circumferential surface of the welded portion of said piping such that they are put between said current input-output electrodes;
    an electric alternating current power supply for alternately supplying an alternating current of a frequency of either 10 Hz or less or 50 Hz or greater between said current input-output electrodes of said sensor head;
    a crack electric potential difference measurement means for measuring an electric potential difference between said crack electric potential difference measuring electrodes of said sensor head;
    an intra-crack electric potential difference correction means for correcting the electric potential difference between said crack electric potential difference measuring electrodes of said sensor head measured by said crack electric potential difference measurement means; and
    a crack length calculation means for calculating the length of said crack on the basis of said electric potential difference obtained by said intra-crack electric potential difference correction means.

12. A crack monitoring apparatus according to claim 11, wherein the positions of said current input-output electrodes and those of the crack electric potential difference measuring electrodes of said sensor head are set on the basis of an electric field analysis of the welded portion of the piping surrounding said crack in said piping so that the electric potential difference can be measured most sensitively at the growth of said crack on said piping.

13. A crack monitoring apparatus according to claim 12, wherein said pair of crack electric potential difference measuring electrodes of said sensor head are attached to the piping such that the crack on the center side is put between the electrodes in a direction perpendicular to the direction of likely growth of said crack in said piping.

14. A crack monitoring apparatus according to claim 13, wherein the other pair of said crack electric potential difference measuring electrodes of said sensor head are attached to the piping such that the crack on the tip side thereof in the direction of likely growth is put between the electrodes in a direction perpendicular to the direction of likely growth of said crack in said piping.

15. A crack monitoring apparatus according to claim 11, wherein there is provided an attachment means for removably attaching said sensor head to the outer circumferential surface of said piping.

16. A crack monitoring apparatus according to claim 11, wherein said intra-crack electric potential difference correction means comprises a pair of correction electric potential difference measuring electrodes made of heat-resistant material arranged in said sensor head so as to be attached to the outer circumferential surface of said piping and a correction electric potential difference measurement means for measuring an electric potential difference between said correction electric potential difference measuring electrodes.

17. A crack monitoring apparatus according to claim 11, wherein said intra-crack electric potential difference correction means comprises a piping temperature measurement means for measuring the temperature of said piping.

18. A crack monitoring apparatus according to claim 11, wherein said intra-crack electric potential difference correction means comprises a piping pressure measurement means for measuring the internal pressure of said piping.

19. A crack monitoring apparatus according to claim 11, wherein said crack length calculation means calculate the length of the crack from said electric potential difference obtained by said intra-crack electric potential difference correction means on the basis of a correlation between the length of the crack obtained from an electric field analysis of the welded portion surrounding the crack in said piping or experimentally and the electric potential difference in the crack.

20. A crack monitoring apparatus according to claim 11, wherein said crack length calculation means performs:
    a first step of obtaining a correlation between the maximum crack length of said crack for each stress change and an electric potential difference change in the crack on the basis of the electric field analysis of the welded portion surrounding said crack in said piping or experimentally;
    a second step of obtaining a stress change between two points in time, that is, the time when a high load is applied and the time when a low load is applied on the piping on the basis of the temperature and the internal pressure of said piping; and a third step of obtaining the length of said crack corresponding to the stress change from the electric potential difference change between said two points in time.

21. A crack monitoring apparatus according to claim 11, wherein:

a plurality of said sensor heads are arranged;

said intra-crack electric potential difference measurement means measures electric potential differences between said crack electric potential difference measuring electrodes of each of said plurality of the sensor heads;

said intra-crack electric potential difference correction means corrects the electric potential differences between said crack electric potential difference measuring electrodes of each of said plurality of sensor heads measured by said crack electric potential difference measurement means; and said crack length calculation means calculates the lengths of each of the cracks on the basis of the electric potential differences obtained by said intra-crack electric potential difference correction means.

22. A crack monitoring apparatus according to claim 11, wherein said intra-crack electric potential difference measurement means, said intra-crack electric potential difference correction means, and said crack length calculation means are arranged in a remote area far from said piping.

* * * * *